United States Patent
Hirayama

(10) Patent No.: US 12,171,404 B2
(45) Date of Patent: Dec. 24, 2024

(54) ENDOSCOPE

(71) Applicant: HOYA CORPORATION, Tokyo (JP)

(72) Inventor: Tetsu Hirayama, Tokyo (JP)

(73) Assignee: HOYA CORPORATION, Tokyo (JP)

(*) Notice: Subject to any disclaimer, the term of this patent is extended or adjusted under 35 U.S.C. 154(b) by 371 days.

(21) Appl. No.: 17/765,678

(22) PCT Filed: Sep. 30, 2020

(86) PCT No.: PCT/JP2020/037102
§ 371 (c)(1),
(2) Date: Mar. 31, 2022

(87) PCT Pub. No.: WO2021/070697
PCT Pub. Date: Apr. 15, 2021

(65) Prior Publication Data
US 2022/0287585 A1    Sep. 15, 2022

(30) Foreign Application Priority Data

Oct. 10, 2019   (JP) ................... 2019-187020

(51) Int. Cl.
*A61B 1/005* (2006.01)
*A61B 5/06* (2006.01)
(Continued)

(52) U.S. Cl.
CPC ............ *A61B 1/005* (2013.01); *A61B 5/06* (2013.01); *A61B 8/12* (2013.01); *A61B 34/20* (2016.02)

(58) Field of Classification Search
CPC ... A61B 1/0011; A61B 1/018; A61B 1/00071; A61B 1/005; A61B 1/012; A61B 1/00119
See application file for complete search history.

(56) References Cited

U.S. PATENT DOCUMENTS

| | | | |
|---|---|---|---|
| 4,280,500 A * | 7/1981 | Ono | A61M 25/0662 128/DIG. 21 |
| 9,439,555 B2 * | 9/2016 | Horne, Jr. | A61B 1/018 |

(Continued)

FOREIGN PATENT DOCUMENTS

| | | |
|---|---|---|
| JP | 07-001630 | 1/1995 |
| JP | 2001-046314 | 2/2001 |

(Continued)

OTHER PUBLICATIONS

International Search Report issued in International Bureau of WIPO Patent Application No. PCT/JP2020/037102, dated Nov. 17, 2020, along with an English translation thereof.

(Continued)

*Primary Examiner* — Alexandra L Newton
(74) *Attorney, Agent, or Firm* — GREENBLUM & BERNSTEIN, P.L.C.

(57) ABSTRACT

Pliability of a tube is ensured while preventing deformation of the tube, occurrence of air leakage, and the like. An endoscope includes an insertion portion and a tube arranged inside the insertion portion. The insertion portion includes a bending section that is bendable based on an operation, a distal tip connected to a distal tip of the bending section, and a flexible tube portion that is bendable by external force independent of the operation. The tube includes an inner layer and an outer layer formed outside the inner layer. The inner layer is formed from polytetrafluoroethylene having solid structure. The outer layer is positioned at an end portion on a side of the distal tip and includes a first portion formed from polytetrafluoroethylene having solid structure and a second portion formed from polytetrafluoroethylene having porous structure.

8 Claims, 6 Drawing Sheets

(51) Int. Cl.
*A61B 8/12* (2006.01)
*A61B 34/20* (2016.01)

(56) References Cited

U.S. PATENT DOCUMENTS

| | | |
|---|---|---|
| 2010/0256445 A1 | 10/2010 | Fitzpatrick |
| 2019/0246885 A1* | 8/2019 | Karikomi ............... A61B 1/015 |
| 2020/0046202 A1 | 2/2020 | Morishima et al. |
| 2020/0100655 A1 | 4/2020 | Morishima et al. |
| 2022/0110506 A1 | 4/2022 | Morishima et al. |

FOREIGN PATENT DOCUMENTS

| | | | |
|---|---|---|---|
| WO | 2008/088087 | 7/2008 | |
| WO | 2016/052208 | 4/2016 | |
| WO | WO-2018088087 A1 * | 5/2018 | ......... A61B 1/00066 |
| WO | 2018/220867 A1 | 6/2018 | |

OTHER PUBLICATIONS

Communication Under Rule 71(3) in related European application No. 20873553.0, dated Dec. 8, 2023.
Extended European Search Report issued in related EP application No. 20873553.0, dated Sep. 7, 2023.

* cited by examiner

ENDOSCOPE

TECHNICAL FIELD

The present invention relates to an endoscope.

BACKGROUND ART

An endoscope device generally includes an insertion portion to be inserted into a body of a subject (such as a digestive organ). The insertion portion internally includes a light guide used for transmitting light and an electric wiring used for transmitting an electric signal from an imaging unit. In addition, the insertion portion internally includes an air and water supply tube used for supplying water or air, and a tube for a treatment tool in/from which a treatment tool may be inserted and removed.

In a case where such a tube is connected to the distal tip of the endoscope, it is desirable to connect them such that the strength of the tube is not degraded, the outer shape is not deformed, and a step is not formed on the inner surface. It is also required to prevent air leakage due to breakage of the tube or the like. On the other hand, it is desirable that various tubes are pliably deformable.

It has been difficult for endoscopes that have been conventionally proposed to satisfy the above-mentioned demands for various tubes. For example, in Patent Literature 1, since structure in which a tube is fitted outside a pipe member is adopted, the outer diameter of the tube is larger and the tube is deformed at a part connected to the pipe member (end portion), leading to an issue that the physical strength of the deformed part is degraded.

On the other hand, in Patent Literature 2, in the structure in which a tube is fitted outside a pipe member similarly, the tube has two-layer structure, and an inner layer is formed from polytetrafluoroethylene (PTFE) having solid structure, and the end portion of an outer layer that is a part to be connected is formed from polytetrafluoroethylene (PTFE) having porous structure. Since the end portion has porous structure, the fitting operation can be performed using smaller force when the tube is fitted outside the pipe member. However, even in this structure, deformation of the outer diameter of the tube is inevitable, and the issue that the physical strength is degraded still occurs.

CITATION LIST

Patent Literature

Patent Literature 1: JP 7-1630 A
Patent Literature 2: WO 2008/088087 A

SUMMARY OF INVENTION

Technical Problem

An object of the present invention is to provide an endoscope capable of ensuring pliability of a tube while preventing deformation of the tube, occurrence of air leakage, and the like.

Solution to Problem

In order to solve the above-mentioned issue, an endoscope according to the present invention includes an insertion portion and a tube arranged inside the insertion portion. The insertion portion includes a bending section that is bendable based on an operation, a distal tip connected to a distal tip of the bending section, and a flexible tube portion that is bendable by external force independent of the operation, in which the tube includes an inner layer and an outer layer formed outside the inner layer. The inner layer is formed from polytetrafluoroethylene having solid structure, and the outer layer is positioned at an end portion on a side of the distal tip and includes a first portion formed from polytetrafluoroethylene having solid structure and a second portion formed from polytetrafluoroethylene having porous structure.

Advantageous Effects of Invention

According to an endoscope of the present invention, the endoscope capable of ensuring pliability of a tube while preventing deformation of the tube, occurrence of air leakage, and the like can be provided.

DESCRIPTION OF EMBODIMENTS

Hereinafter, the present embodiments will be described with reference to accompanying drawings. In the accompanying drawings, functionally identical elements may be represented by the same number. Note that, although the accompanying drawings illustrate the embodiments and implementation examples conforming to the principles of the present disclosure, these are for understanding the present disclosure and are not used to interpret the present disclosure in a limited manner. The description in this specification is merely exemplary and is not intended to limit the scope of the claims or the application of the present disclosure in any way.

In the present embodiments, the description is made in sufficient detail for those skilled in the art to make and use the present disclosure, but it is necessary to understand that other implementations and embodiments are possible, and changes in configurations and structure and replacement of various elements are possible without departing from the scope and the spirit of the technical idea of the present disclosure. Therefore, the following description should not be interpreted to limit the present disclosure thereto.

First Embodiment

First, an endoscope system according to a first embodiment of the present invention will be described in detail.

Figure 1:
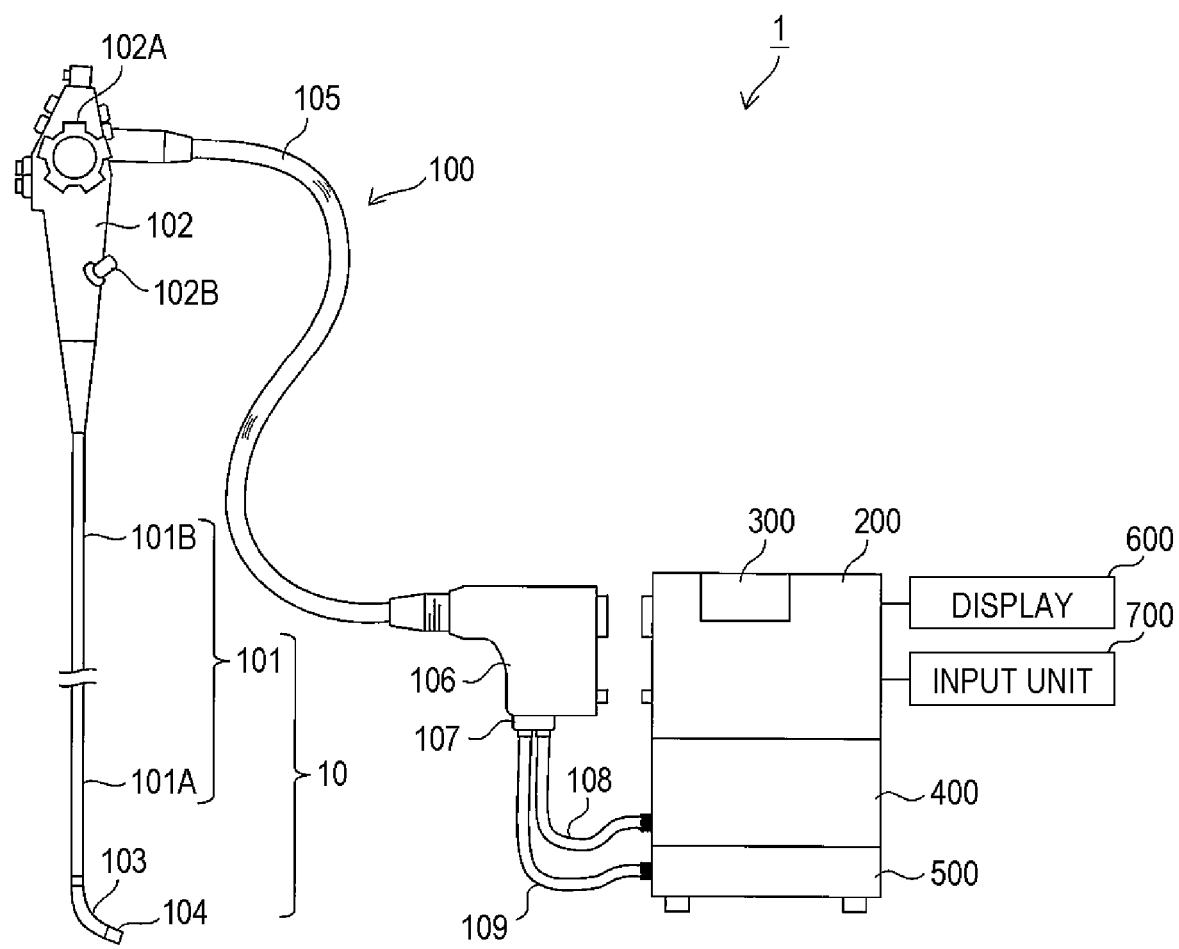
FIG. 1 is an external view of an endoscope system 1 according to a first embodiment of the present invention.
Figure 2:
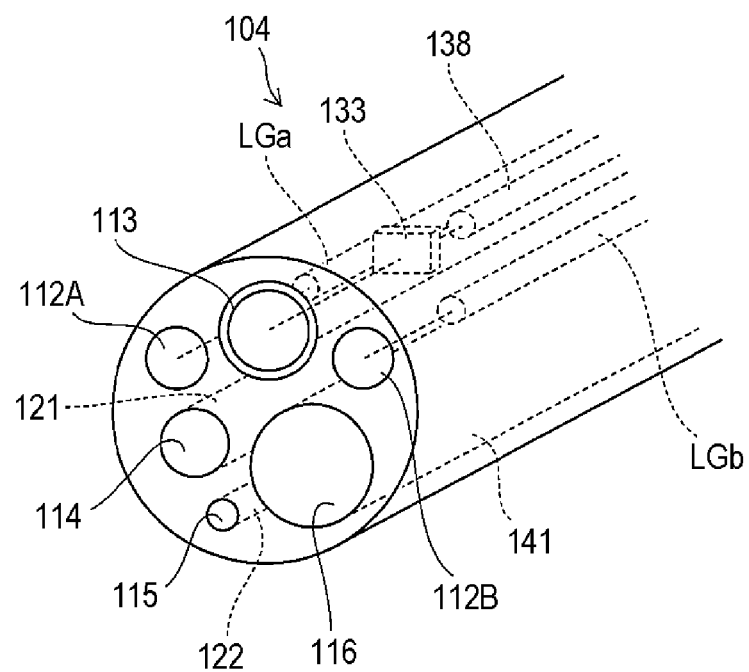
FIG. 2 is a schematic perspective view illustrating structure of a distal tip 104 part of an endoscope 100.

FIG. 1 is an external view of an endoscope system 1 according to the first embodiment, and FIG. 2 is a perspective view illustrating structure of a distal tip 104 of an endoscope 100. The endoscope system 1 substantially includes the endoscope 100, a processor 200, a light source device 300, a water and air supply unit 400, a suction unit 500, a display 600, and an input unit 700.

The endoscope 100 is configured to be insertable into a body of a subject and has a function of imaging an object and transmitting an image signal of the image captured by the imaging to the processor 200. The processor 200 receives the image signal from the endoscope 100 and performs predetermined signal processing.

The light source device 300 is configured to be connectable to the processor 200, and internally includes a light source that emits irradiation light used for irradiating an object. The light from the light source is emitted toward a subject through light guides to be described below. The light source device 300 may be configured separately from the processor 200 and configured to be connectable to the processor 200, or may be incorporated inside the processor 200.

The water and air supply unit 400 includes an air pump and a water flow pump (not illustrated) used for discharging a water flow or an air flow supplied to a subject. The suction unit 500 includes a pump and a tank (not illustrated) used for sucking a body fluid or an excision sucked from a body of a subject through an insertion portion 10.

The display 600 is a display device for displaying based on, for example, result of data processing by the processor 200. The input unit 700 is a device for inputting an instruction from an operator in various measurement operations.

The endoscope 100 includes the insertion portion 10, a hand operation unit 102, a universal cable 105, and a connector unit 106. The insertion portion 10 includes a flexible tube portion 101, a connecting portion 103A, a bending section 103, and the distal tip 104.

As illustrated in FIG. 1, the insertion portion 10 of the endoscope 100 has flexibility and includes the flexible tube portion 101 to be inserted into a body of a subject. One end of the flexible tube portion 101 is connected to the hand operation unit 102. The hand operation unit 102 includes, for example, a bending operation knob 102A and other operation units that can be operated by a user, and is a portion for allowing an operator to perform various operations for imaging by the endoscope system 1. Note that the hand operation unit 102 includes a treatment tool insertion port 102B through which a treatment tool may be inserted.

Of the flexible tube portion 101, a portion close to the bending section 103 is a first flexible tube portion 101A, and a portion close to the hand operation unit 102 is a second flexible tube portion 101B. While the shape of the bending section 103 can be actively changed by an operation of the bending operation knob 102A by an operator, the first flexible tube portion 101A is a portion having a shape that is passively changed by external force independent of the operation of the bending operation knob 102A, for example, external force caused by the distal tip 104 or the bending section 103 hitting the wall surface of a digestive organ. The same applies to the second flexible tube portion 101B, but the degree of change in shape is smaller (the maximum curvature radius is larger) than that of the first flexible tube portion 101A. Note that, in the example of FIG. 1, the flexible tube portion 101 includes two types of flexible tube portions, but the present invention is not limited thereto, and three or more types of flexible tube portions may be provided, or one type may be provided.

At the distal tip of the flexible tube portion 101, a bending section 103 (active bending section) configured to be bendable is provided. As described above, the bending section 103 is bent by being pulled by an operation wire (not illustrated in FIG. 1) linked with a rotation operation of the bending operation knob 102A provided on the hand operation unit 102. Note that a connecting portion that is not deformed by bending wires W or external force may be provided between the bending section 103 and the first flexible tube portion 101A.

To the distal tip of the bending section 103, the distal tip 104 including an image sensor (imaging unit) is connected. Change of the direction of the distal tip 104 according to a bending operation of the bending section 103 by a rotation operation of the bending operation knob 102A can change the imaging region by the endoscope 100.

From the opposite side of the hand operation unit 102, the universal cable 105 extends toward the connector unit 106. Similarly to the insertion portion 10, the universal cable 105 internally includes the light guides, various wirings, and various tubes.

The connector unit 106 includes various connectors for connecting the endoscope 100 to the processor 200. In addition, the connector unit 106 includes a water and air supply tube 108 as a path through which a water flow and an air flow are sent toward the insertion portion 10.

The structure of the distal tip 104 of the endoscope 100 will be described with reference to FIG. 2. Light distribution lenses 112A and 112B are arranged on the distal tip 104 of the endoscope 100, and light guides LGa and LGb extend from the distal tip 104 to the connector unit 106 inside the flexible tube portion 101. Light from the light source of the light source device 300 is guided by the light guides LGa and LGb, and is emitted toward a subject by the light distribution lenses 112A and 112B arranged on the distal tip 104.

Furthermore, as illustrated in FIG. 2, the endoscope 100 includes an objective lens 113 and an image sensor 133 in the distal tip 104. The objective lens 113 provided on the distal tip 104 condenses scattered light or reflected light from a subject to form an image of the subject on the light receiving surface of the image sensor 133.

The image sensor 133 may be formed by using, for example, a charge coupled device (CCD) or a complementary metal oxide semiconductor sensor (CMOS sensor). The image sensor 133 is controlled by a signal (gain control signal, exposure control signal, shutter speed control signal, and the like) supplied from the processor 200 via an electric wiring 138, and supplies an image signal of a captured image to the processor 200 via the electric wiring 138 and an A/D conversion circuit (not illustrated).

In addition, on the end surface of the distal tip 104, an air and water supply port 114 (nozzle), a sub water supply port 115, and a treatment tool port 116 are provided as end portions or openings of various tubes. The air and water supply port 114 is connected to an air and water supply tube 121 in order to introduce a water flow or an air flow used for, for example, cleaning the distal tip 104.

The sub water supply port 115 is connected to a sub water supply tube 122 in order to introduce a sub water supply used for removing wastes in the field of view. The tubes 121 and 122 are arranged such that they extend along the inside of the distal tip 104, the bending section 103, the flexible tube portion 101, the hand operation unit 102, and the universal cable 105.

In addition to such tubes 121 and 122, a treatment tool tube 141 is provided inside the endoscope 100. The treatment tool tube 141 is arranged such that a treatment tool such as forceps can be freely moved forward and backward inside the treatment tool tube 141. The distal tip of the treatment tool tube 141 forms the treatment tool port 116 in the distal tip 104.

Figure 3:
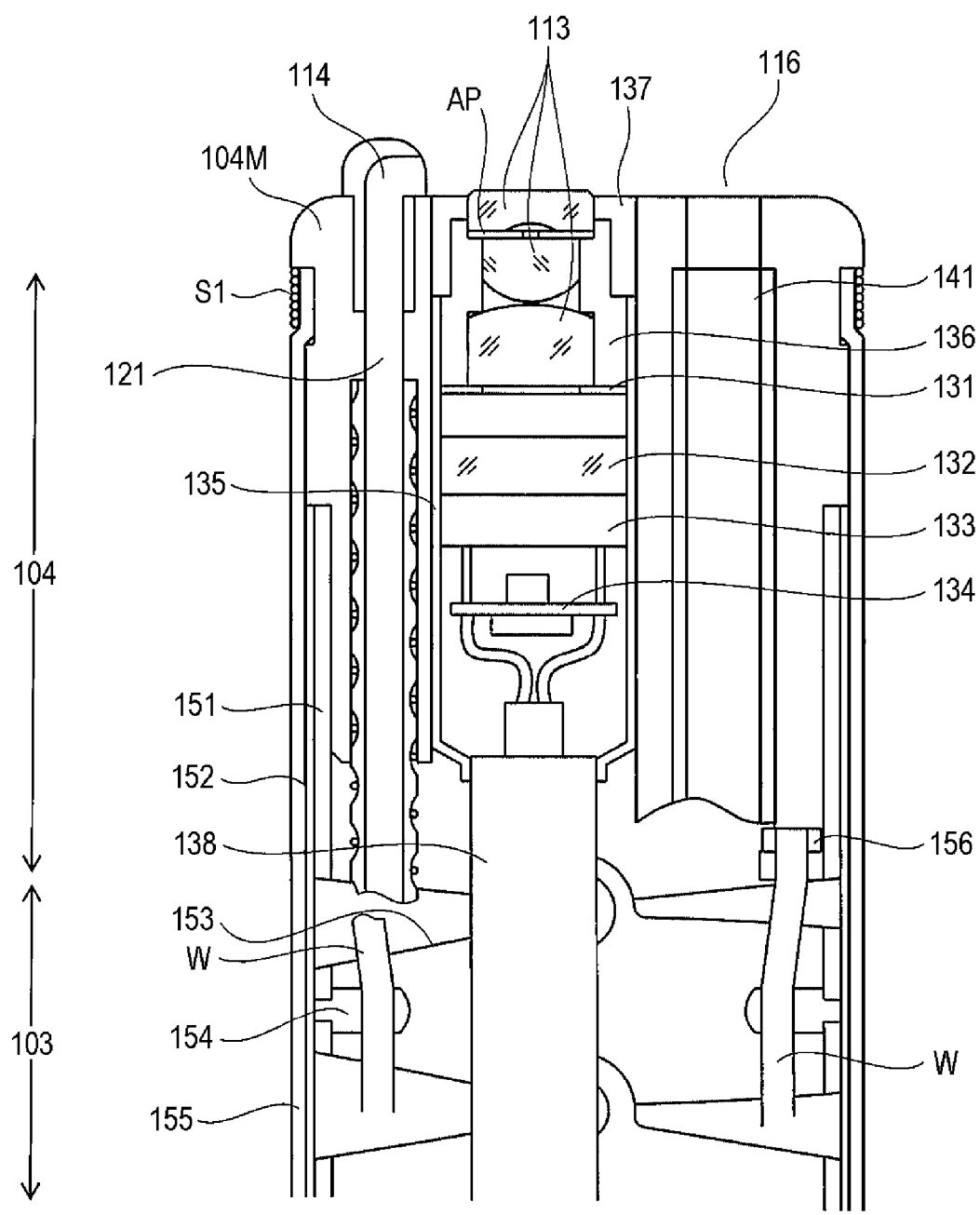
FIG. 3 is a cross-sectional view illustrating cross-sectional structure of the distal tip 104 in detail.

The cross-sectional structure of the distal tip 104 will be described in more detail with reference to FIG. 3. This cross-sectional view illustrates details of the structure of the objective lens 113 to the electric wiring 138, the air and water supply tube 121, and the treatment tool tube 141. The structure of the light distribution lenses 112A and 112B and the light guides LGa and LGb are not illustrated. The structure of the sub water supply tube 122 is also not illustrated.

The distal tip 104 includes a distal-end rigid portion 104M. The distal-end rigid portion 104M includes hole portions forming the air and water supply port 114, the sub water supply port 115, and the treatment tool port 116 described above. As illustrated in FIG. 3, the air and water supply tube 121 and the treatment tool tube 141 are inserted into corresponding hole portions of the distal-end rigid portion 104M.

The distal-end rigid portion 104M also includes a hole portion into which a lens frame 136 holding the objective lens 113, a diaphragm AP, and a light-shielding mask 131 is fitted. The lens frame 136 is fixed into the hole portion of the distal-end rigid portion 104M via a sealant 137.

On the other hand, for example, the light-shielding mask 131, a cover glass 132, the image sensor (CCD) 133, and a circuit board 134 are held behind the objective lens 113 by a CCD unit frame 135, and the CCD unit frame 135 is inserted and fixed into the hole portion of the distal-end rigid portion 104M. The electric wiring 138 is connected to the circuit board 134.

The distal tip 104 (distal-end rigid portion 104M) formed as described above is fitted to the distal tip of the bending section 103. The bending section 103 includes bending pieces 153 formed in a substantially cylindrical shape connected to each other in a rotatable manner by rivets. The outer surfaces of the bending pieces 153 are covered with a reticular tube 152. The end portion of the reticular tube 152 is joined to the distal-end rigid portion 104M through an adjoining annular tube 151. The outer surface of the reticular tube 152 is covered with a synthetic resin outer cover rubber tube 155. The end portions of the outer cover rubber tube 155 and the distal-end rigid portion 104M are fixed by, for example, a fixing string S1.

Wire guides 154 are provided between a plurality of the bending pieces 153, and the bending wires W used for a bending operation pass through the wire guides 154. For example, the number of the bending wires W is four and the four bending wires W are provided at substantially equal intervals in the circumferential direction in one flexible tube portion 101. An end of each of the bending wires W is fixed to the front-most bending piece 153. The bending section 103 is bent when the other end of each of the bending wires W is tensioned or relaxed by the operation of the bending operation knob 102A.

Figure 4:
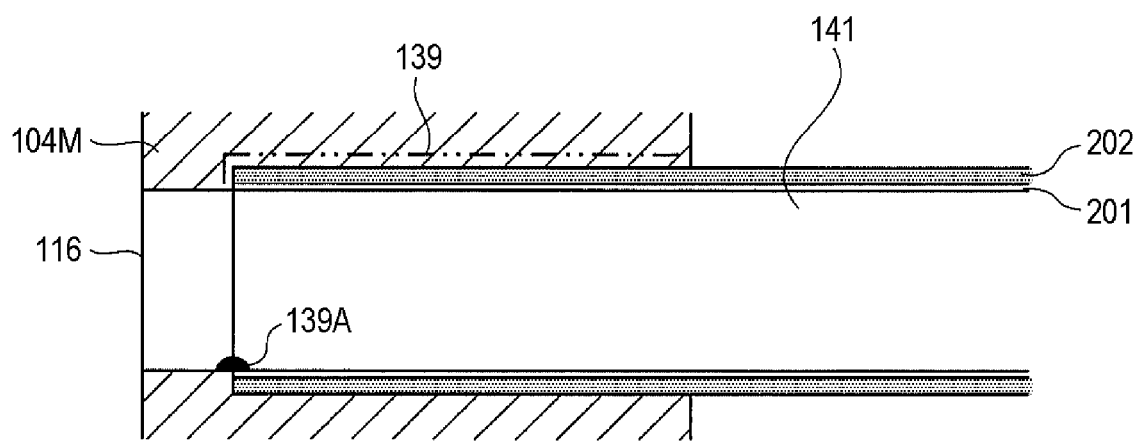
FIG. 4 is a cross-sectional view illustrating an example of structure of a treatment tool tube 141 according to a comparative example.
Figure 5:
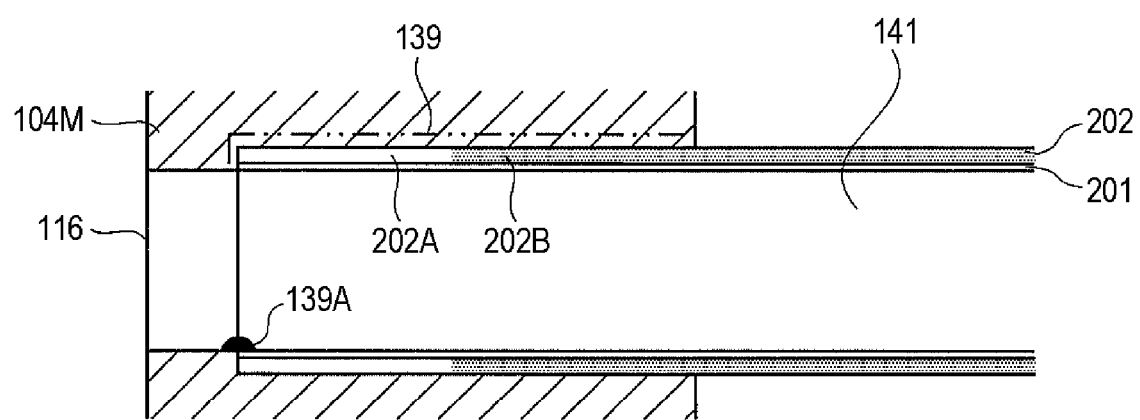
FIG. 5 is a cross-sectional view illustrating an example of structure of a treatment tool tube 141 according to the first embodiment.

An example of structure of the treatment tool tube 141 will be described with reference to FIG. 4 and FIG. 5. FIG. 4 is a cross-sectional view illustrating an example of structure of a treatment tool tube 141 according to a comparative example, and FIG. 5 is a cross-sectional view illustrating an example of structure of the treatment tool tube 141 according to the first embodiment.

The treatment tool tube 141 of the comparative example in FIG. 4 has two-layer structure of an inner layer 201 and an outer layer 202 outside the inner layer. The inner layer 201 is formed from polytetrafluoroethylene (PTFE) having solid structure over the entire length (from the distal tip 204 to the hand operation unit 102), and the outer layer 202 is formed from polytetrafluoroethylene (PTFE) having porous structure over the entire length. The treatment tool tube 141 is inserted into a hole portion formed in a size corresponding to the outer diameter of the treatment tool tube 141 in the distal-end rigid portion 104M. An adhesive 139 is applied between the outer surface of the treatment tool tube 141 and the inner wall of the hole portion, and the treatment tool tube 141 is fixed into the distal-end rigid portion 104M using this adhesive 139.

In a case where such treatment tool tube 141 having two-layer structure of PTFE having solid structure and PTFE having porous structure is inserted into the hole portion of the distal-end rigid portion 104M of the distal tip 104 and fixed using the adhesive 139, the treatment tool tube 141 can be fixed without the outer shape being deformed. Since the outer layer 202 is formed from PTFE having porous structure over the entire length, pliability of the tube can also be ensured.

However, in a case of the structure of the comparative example in FIG. 4, when protrusion of an adhesive 139A occurs at the end portion of the treatment tool tube 141, there is an issue that removal of the protrusion is hindered. In a case where such protrusion of the adhesive 139A occurs, removal of the protrusion using a tool may be necessary. However, the inner layer 201 may be damaged in the process of the removal, and the outer layer 202 may be exposed. In this case, there is a possibility that air leakage from the exposed part of the outer layer 202 occurs.

In a case of the structure in FIG. 4, the adhesive 139 needs to be applied to the end portion of the treatment tool tube 141 to prevent air leakage from the end portion of the treatment tool tube 141. For this reason, avoiding such protrusion of the adhesive 139A is difficult.

Meanwhile, similarly to the comparative example, an outer layer 202 of the treatment tool tube 141 of the first embodiment has two-layer structure of an inner layer 201 and the outer layer 202 outside the inner layer. Similarly to the comparative example, the inner layer 201 is formed from PTFE having solid structure over the entire length.

However, as for the outer layer 202, unlike the comparative example, a first portion 202A positioned at the end portion of the treatment tool tube 141 is formed from PTFE having solid structure. A second portion 202B described lastly is formed from PTFE having porous structure. In other words, both the inner layer 201 and the outer layer 202 are formed from PTFE having solid structure at the end portion of the treatment tool tube 141.

According to the configuration of the first embodiment, even if protrusion of the adhesive 139A occurs, there is no possibility that the air leakage occurs as in the comparative example. Similarly to the inner layer 201, the outer layer 202 at the end portion of the treatment tool tube 141 is formed from PTFE having solid structure. Therefore, in the process of removal of the adhesive 139A, even if the inner layer 201 at the end portion is damaged, the air leakage does not occur because the outer layer 202 is PTFE having solid structure.

On the other hand, the outer layer 202 excluding the end portion (second portion 202B) is formed from PTFE having porous structure, similarly to the comparative example. In a case where the outer layer 202 is formed from PTFE having porous structure, pliability of the treatment tool tube 141 can be increased, and the flexible tube portion 101 can be flexibly deformed according to a shape of a digestive organ.

In addition, the adhesion strength by the adhesive 139 can be increased by an anchor effect, and thus, the treatment tool tube 141 and the distal-end rigid portion 104M can be firmly connected.

As described above, according to the treatment tool tube 141 of the first embodiment, an endoscope capable of ensuring pliability of a tube while preventing deformation of the tube, occurrence of air leakage, and the like can be provided.

Second Embodiment

Next, an endoscope system according to a second embodiment will be described with reference to FIG. 6. The overall configuration of the endoscope system of the second embodiment is substantially the same as that of the first embodiment (FIG. 1 to FIG. 3), and thus duplicate description is omitted below.

Figure 6:
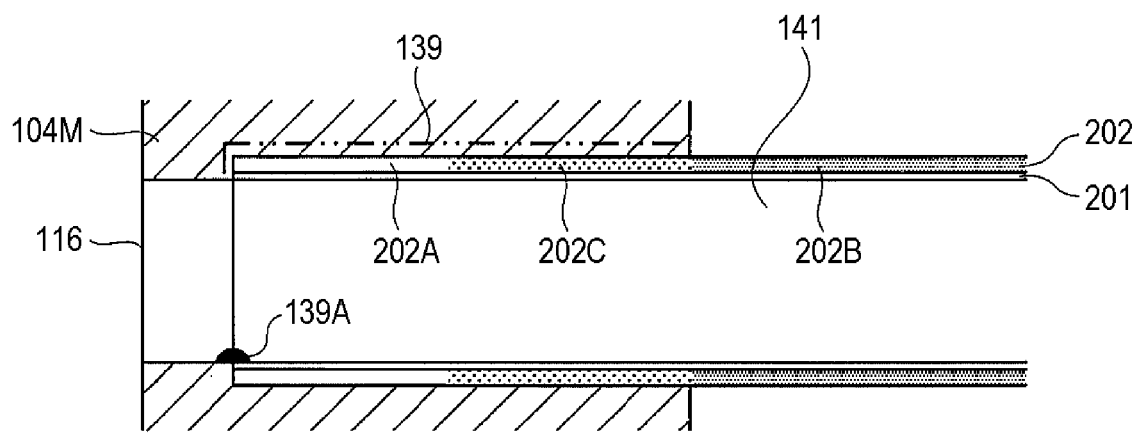
FIG. 6 is a cross-sectional view illustrating an example of structure of a treatment tool tube 141 according to a second embodiment.

As illustrated in FIG. 6, the second embodiment is different from the first embodiment in structure of a treatment tool tube 141. Similarly to the first embodiment, the treatment tool tube 141 includes a first portion 202A formed from PTFE having solid structure and a second portion 202B formed from PTFE having porous structure. However, between the first portion 202A and the second portion 202B, a third portion 202C having porosity that increases toward the second portion 202B (transition portion) is provided. For example, the third portion 202C extends from the inside of the distal-end rigid portion 104M to the vicinity of the inlet of the hole portion of the distal-end rigid portion 104M.

The porosity of the third portion 202C is substantially zero in the vicinity of the first portion 202A, but increases toward the second portion 202B, and is substantially the same as the porosity of the second portion 202B in the vicinity of the second portion 202B. As described above, since the third portion 202C at least in part includes PTFE having porous structure, the anchor effect is produced by the adhesive 139, and the distal-end rigid portion 104M can be firmly connected by the adhesive 139.

The second embodiment can also produce substantially the same effect as that of the first embodiment.

Third Embodiment

Next, an endoscope system according to a third embodiment will be described with reference to FIG. 7. The overall configuration of the endoscope system of the third embodiment is substantially the same as that of the first embodiment (FIG. 1 to FIG. 3), and thus duplicate description is omitted below.

Figure 7:
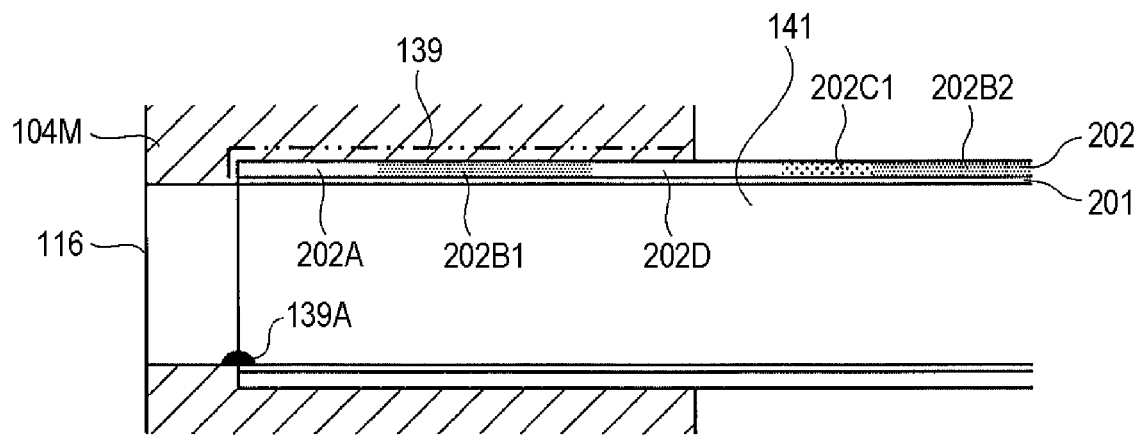
FIG. 7 is a cross-sectional view illustrating an example of structure of a treatment tool tube 141 according to a third embodiment.

As illustrated in FIG. 7, the third embodiment is different from the first embodiment in structure of a treatment tool tube 141. Similarly to the first embodiment, an outer layer 202 of the treatment tool tube 141 includes a first portion 202A formed from PTFE having solid structure, and a second portion 202B2 formed from PTFE having porous structure.

However, the outer layer 202 positioned inside the hole portion of the distal-end rigid portion 104M includes, in order from the distal tip 104 side, the first portion 202A, a fourth portion 202B1 formed from PTFE having porous structure, and a fifth portion 202D formed from PTFE having solid structure. The fifth portion 202D is provided from the front to the rear of the inlet of the hole portion of the distal-end rigid portion 104M, and a part of the fifth portion 202D protrudes outward from the hole portion.

Note that, in the example illustrated in FIG. 7, between the fifth portion 202D and the second portion 202B2, a sixth portion 202C1 having porosity gradually increases is also formed. The sixth portion 202C1 may be omitted, and the fifth portion 202D having solid structure and the second portion having porous structure may be directly connected.

According to the structure of the third embodiment, the first portion 202A is formed from PTFE having solid structure, whereby the same effect as that of the first embodiment can be obtained. In addition, the fourth portion 202B1 formed from PTFE having porous structure can firmly connect the treatment tool tube 141 to the distal-end rigid portion 104M.

Adjacent to the fourth portion 202B1, the fifth portion 202D formed from PTFE having solid structure is formed from the front to the rear of the inlet of the hole portion such that it protrudes from the hole portion, and accordingly, the possibility of occurrence of buckling or the like can be reduced even if bending stress is applied to the treatment tool tube 141.

Figure 8:
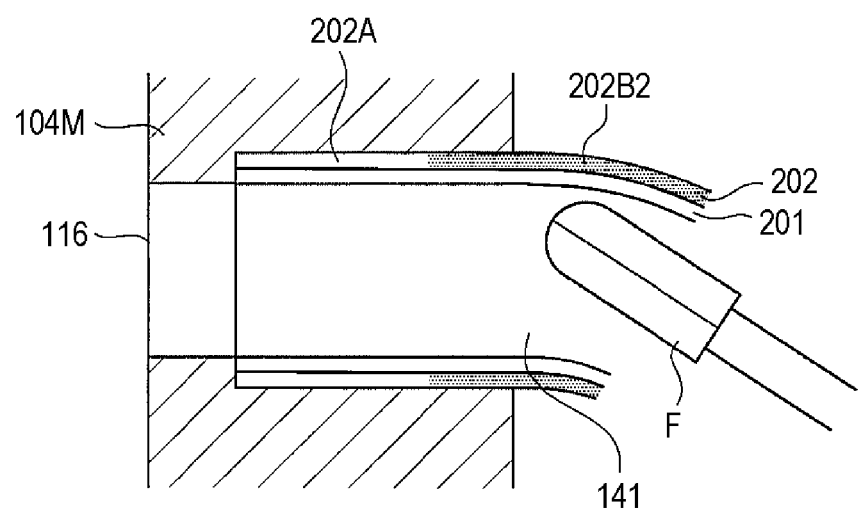
FIG. 8 is a schematic diagram illustrating an effect of the third embodiment.

In addition, since the fifth portion 202D is provided from the front to the rear of the inlet of the hole portion, the treatment tool tube 141 is hardly bent at the root of the hole portion. As illustrated in FIG. 8, in a case where the outer layer 202 from the front to the rear of the inlet of the hole portion is the second portion 202B2 formed from PTFE having porous structure, the treatment tool tube 141 is easily bent from the root of the hole portion. If forceps F entering and exiting the treatment tool tube 141 come into contact with the bent part, there is a possibility that the inner layer 201 is damaged. On the other hand, in the fifth embodiment, since the fifth portion 202D is provided from the front to the rear of the inlet of the hole portion, the treatment tool tube 141 is hardly bent at the root, and breakage of the treatment tool tube 141 can be prevented or reduced.

Others

The present invention is not limited to the above-described embodiments, and includes various modifications. For example, the above-described embodiments have been described in detail in order to describe the present invention in an easy-to-understand manner, and the present invention is not necessarily limited to those having all the described configurations. A part of the configuration of a certain embodiment can be replaced with the configuration of another embodiment, and the configuration of a certain embodiment can be added to the configuration of another embodiment. In addition, another configuration can be added to or deleted from a part of the configuration of each embodiment, or a part of the configuration of each embodiment can be replaced with another configuration.

REFERENCE SIGNS LIST

1 Endoscope system
100 Endoscope
10 Insertion portion
101 Flexible tube portion
101A First flexible tube portion
101B Second flexible tube portion
102 Hand operation unit
102A Bending operation knob
103 Bending section
104 Distal tip
104M Distal-end rigid portion
105 Universal cable 106 Connector unit
108 Water and air supply tube
109 Suction tube
LGa, LGb Light guide
112A, 112B Light distribution lens
113 Objective lens
114 Air and water supply port
115 Sub water supply port
116 Treatment tool port
121 Air and water supply tube
122 Sub water supply tube
141 Treatment tool tube
133 Image sensor
134 Circuit board
135 CCD unit frame
136 Lens frame
137 Sealant
138 Electric wiring
200 Processor
201 Inner layer
202 Outer layer
300 Light source device
400 Water and air supply unit
500 Suction unit
600 Display
700 Input unit.

The invention claimed is:

1. An endoscope comprising:
an insertion portion; and
a tube arranged inside the insertion portion, wherein
the insertion portion includes
   a bending section that is bendable based on an operation
   a distal tip connected to a distal tip of the bending section and
   a flexible tube portion that is bendable by external force independent of the operation,
the tube includes an inner layer and an outer layer formed outside the inner layer,
the inner layer is formed from polytetrafluoroethylene having solid structure,
the outer layer is positioned at an end portion on a side of the distal tip and includes a first portion formed from polytetrafluoroethylene having a solid structure at the distalmost end of the tube, and a second portion formed from polytetrafluoroethylene having a porous structure proximal to the solid structure, and
an adhesive fixed between a distal facing surface of the tube and a proximal facing surface of the distal tip.

2. The endoscope according to claim 1, wherein the distal tip includes a hole portion into which the tube is insertable.

3. The endoscope according to claim 1, wherein the second portion is formed at a position in contact with the distal tip.

4. The endoscope according to claim 1, wherein the outer layer includes, between the first portion and the second portion, a third portion having porosity that increases toward the second portion.

5. The endoscope according to claim 4, wherein the third portion is formed at a position in contact with the distal tip.

6. The endoscope according to claim 1, wherein the outer layer includes, in order from an end portion on a side of the distal tip, the first portion, a fourth portion formed from polytetrafluoroethylene having porous structure, and a fifth portion formed from polytetrafluoroethylene having solid structure.

7. The endoscope according to claim 6, wherein
the fourth portion is formed at a position in contact with the distal tip, and
the fifth portion is formed at a position where the fifth portion protrudes from an inlet of the distal tip.

8. The endoscope according to claim 6, wherein the outer layer includes, between the fifth portion and the second portion, a sixth portion having porosity that increases toward the second portion.

* * * * *